United States Patent [19]
Merrick et al.

[11] Patent Number: 5,348,005
[45] Date of Patent: Sep. 20, 1994

[54] SIMULATION FOR PULSE OXIMETER

[75] Inventors: Edwin B. Merrick, Stow, Mass.; Peter Haas, East Fairfield, Vt.

[73] Assignee: Bio-Tek Instruments, Inc., Winooski, Vt.

[21] Appl. No.: 57,752

[22] Filed: May 7, 1993

[51] Int. Cl.$^5$ ............................................. A61B 5/00
[52] U.S. Cl. ...................................... 128/633; 356/41; 356/243; 250/252.1
[58] Field of Search ................................ 128/633–634, 128/632, 664–667; 73/1 G; 356/39–42, 243; 250/252.1

[56] References Cited

U.S. PATENT DOCUMENTS

| | | | |
|---|---|---|---|
| 4,796,633 | 1/1989 | Zwirkoski | 128/634 |
| 4,823,167 | 4/1989 | Manska et al. | 128/634 X |
| 4,968,137 | 11/1990 | Yount | |
| 4,981,355 | 1/1991 | Higgins | 128/634 X |
| 5,166,517 | 11/1992 | Volgysei | |

Primary Examiner—Angela D. Sykes

[57] ABSTRACT

A method and system for simulating living tissue which is to be monitored by a pulse oximeter that provides red and infrared light flashes, the system including structure for: converting the red and infrared light flashes of the pulse oximeter into electrical signals; modulating the converted electrical signals to provide modulated electrical signals; and converting the modulated electrical signals to light flashes and transmitting the converted light flashes to the pulse oximeter for detection so that the pulse oximeter responds to the converted light flashes as it would to light flashes modulated by a living tissue.

8 Claims, 7 Drawing Sheets

SIMULATION FOR PULSE OXIMETER

FIELD OF THE INVENTION

The present invention generally relates to the field of pulse oximeters, and more particularly, relates to a device and method for testing or calibrating pulse oximeters.

BACKGROUND OF THE INVENTION

The non-invasive monitoring of arterial oxygen saturation ($SaO_2$) by pulse oximetry is used in many clinical applications. For example, $SaO_2$ monitoring is performed during surgery, in critical care situations, for hypoxemia screening, in the emergency room, and in the field. The instruments are small and lightweight, making them ideal for neonatal, pediatric and ambulatory applications. Because this instrument is capable of providing continuous and safe measurements of blood oxygenation non-invasively, the pulse oximeter is widely recognized as one of the most important technological advances in bedside monitoring. In 1986, the American Society of Anesthesiologists recommended pulse oximetry as a standard of care for basic intraoperative monitoring, and in 1988, the Society for Critical Care Medicine recommended that this method be used for monitoring patients undergoing oxygen therapy. The mandatory or voluntary use of pulse oximetry by regulatory agencies and professional organizations is likely to continue.

Because pulse oximeters are small, easy-to-use and readily available, they have become widespread in the last decade. The high costs associated with health care make the use of non-invasive pulse oximetry very attractive as it permits effective oxygen monitoring without the expensive clinical laboratory analysis of blood samples.

Figure 1:
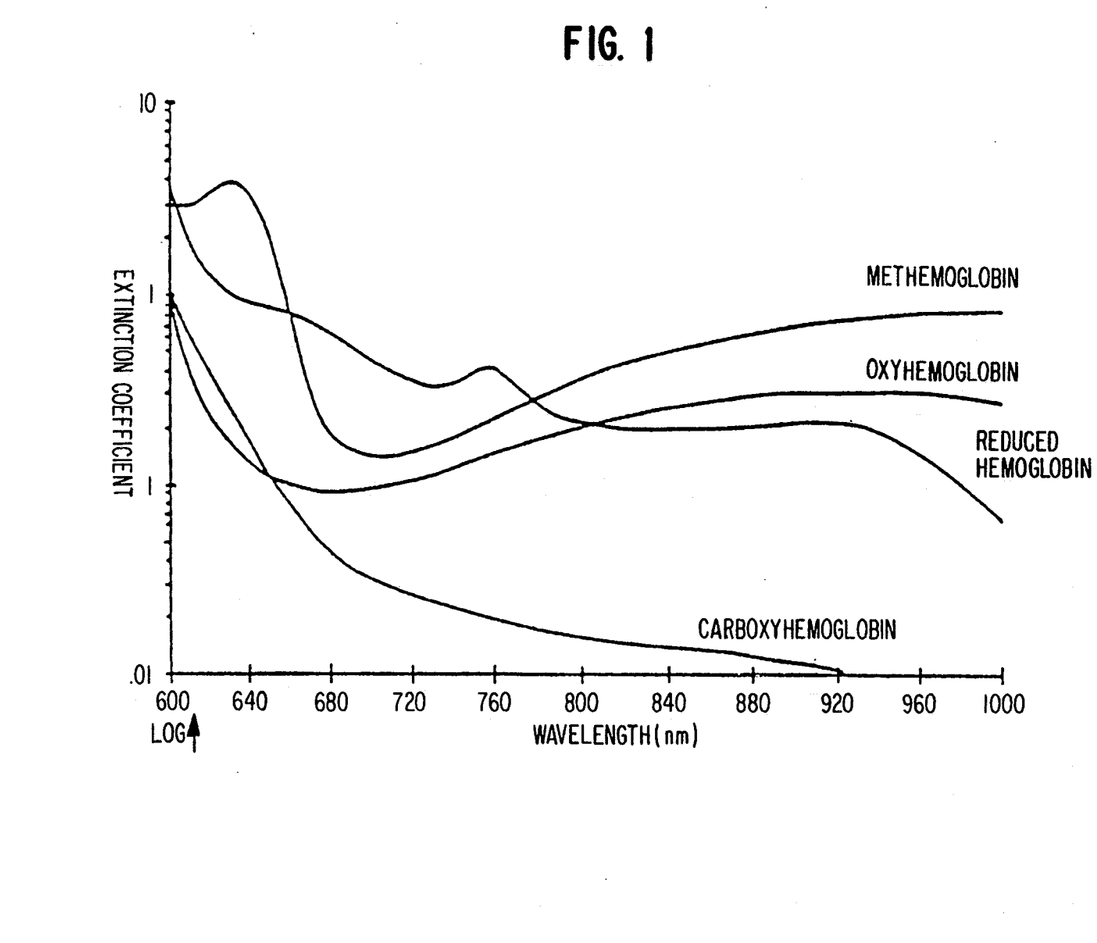
FIGS. 1–3 are graphs for explaining the principles of pulse oximetry.

Oxygen saturation measurements rely on the difference in optical absorbance of deoxyhemoglobin (Hb) and oxyhemoglobin ($HbO_2$), as shown in FIG. 1. $HbO_2$ absorbs less light in the red region (ca. 660 nm) than does Hb, but absorbs more strongly in the infrared region (ca. 940 nm). If both wavelengths of light are used, their opposite change in light absorbed as $HbO_2$ varies versus Hb produces a sensitive index of blood oxygen saturation. The "functional hemoglobin saturation" is defined as:

$$\text{Functional } SaO_2 = \{[HbO_2]/[HbO_2 + Hb]\} \times 100\% \quad (1)$$

Figure 2:
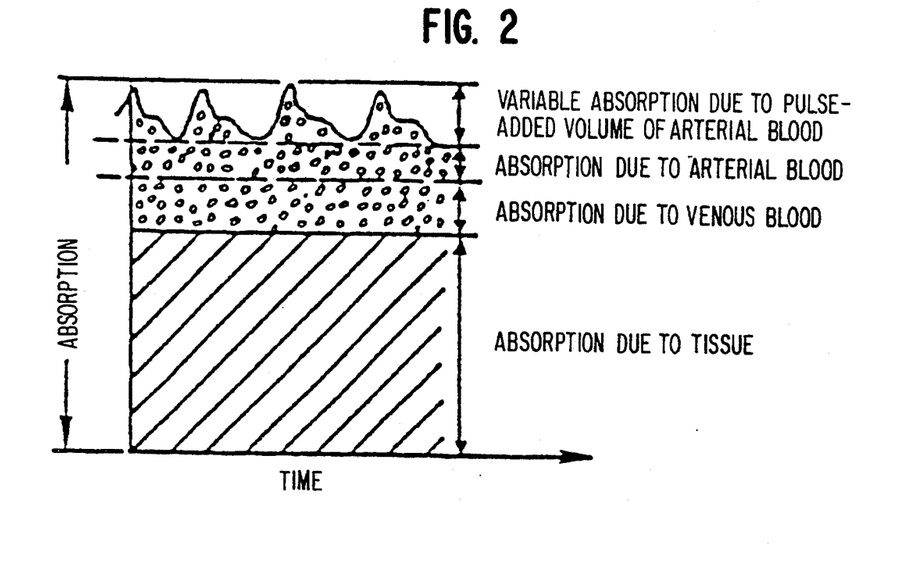

Pulse oximeters thus employ two discrete wavelengths of light, which are passed through a given tissue (typically a finger). The amount of transmitted light for each wavelength is detected and subtracted from the incident light to determine the amount absorbed. From the ratio (R/IR or "red/infrared") of the amount of light absorbed at each wavelength, the blood oxygen saturation is calculated from a predetermined algorithm. If these were the only conditions of the measurement, the calculated saturation value would in some degree reflect the mixture of arterial and venous blood flowing through the tissue. However, in pulse oximetry the time-variant photoplethysmographic signal, caused by increases in arterial blood volume due to cardiac contraction, is used to determine the arterial blood oxygen saturation (FIG. 2). The advantage of this method is that the oxygen saturation values of the relatively constant flow of arterial and venous blood, as well as the constant absorption of light by the tissue, are discarded.

The $SaO_2$ values are derived by analyzing only the changes in absorbance caused by the pulsating arterial blood at a red wavelength (e.g., 660 nm), where the absorbance of $HbO_2$ is less than that of Hb, and a second reference infrared wavelength (e.g., 940 nm), where the absorbance of $HbO_2$ is slightly larger than Hb. Because the transmitted light intensities depend on the sensitivity of the detector and the individual intensities of the light sources (light-emitting diodes, or LEDs), and because tissue absorption can vary a great deal between individuals, a normalization procedure is commonly used. This normalization involves dividing the pulsatile (AC) component of the red and infrared photoplethysmograms (which is a result of the expansion and relaxation of the arterial blood) by the corresponding non-pulsatile (DC) component of the photoplethysmogram (which is due to the absorption of light by tissue, non-pulsatile arterial blood, and venous blood). This scaling process results in a normalized red/infrared ratio (R/IR) which is virtually independent of the incident light intensity. R/IR can thus be expressed as:

$$R/IR = [AC_{red}/DC_{red}]/[AC_{ir}/DC_{ir}] \quad (2)$$

Figure 3:
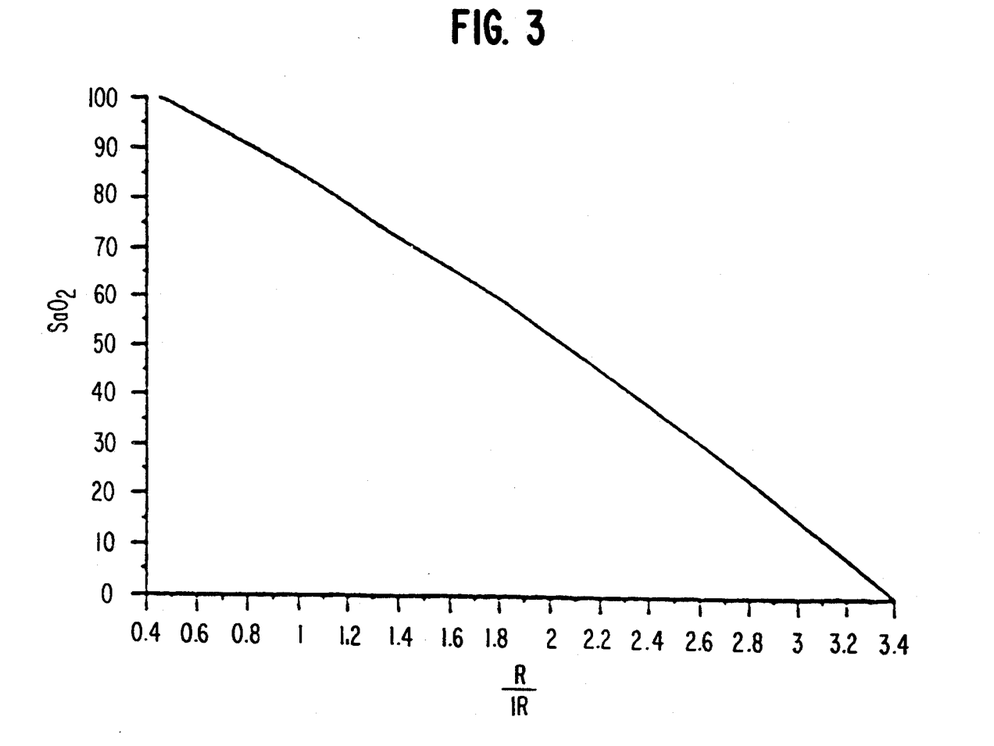

Pulse oximeters are calibrated empirically by correlating the measured ratio of normalized AC/DC signals from the red and infrared photoplethysmograms with blood $SaO_2$ values obtained from a standard in vitro oximeter. A typical relationship between the normalized R/IR ratio and $SaO_2$ is shown in FIG. 3. At approximately 85% $SaO_2$, the amount of light absorbed by Hb and $HbO_2$ is nearly the same, so the normalized amplitudes of the red and infrared signals are equal, and R/IR is 1. For properly functioning instruments, further calibration should not be required in the field because the optical properties of blood are fairly similar among different individuals.

Figure 4:
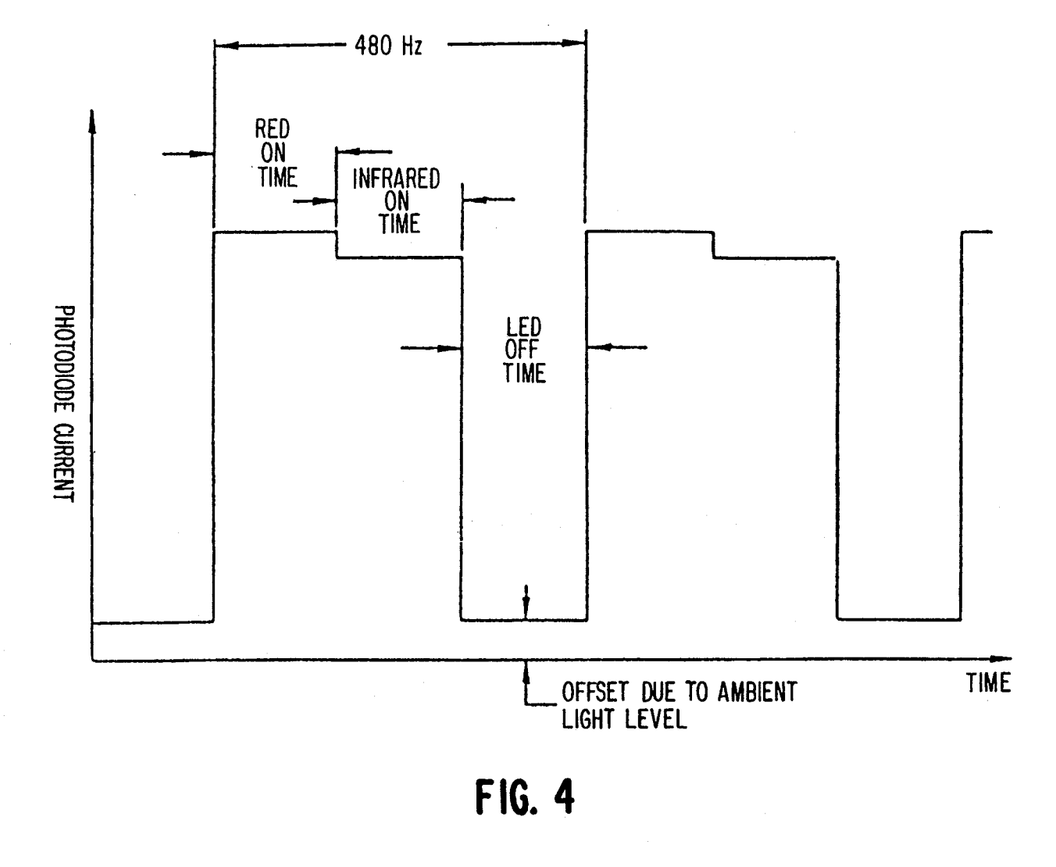
FIG. 4 is a graph for explaining the output of a photodetector on a known pulse oximeter.

Pulse oximeter probes consist of LEDs for two separate and discrete wavelengths (e.g., 660 and 940 nm) and a photodiode light detector. Three different light levels are measured by the photodiode: the red (660 nm) light level, the infrared (940 nm) light level, and the ambient light level. These three light sources are detected separately by a single photodiode by sequencing the red and infrared light sources on and off, allowing an interval when both are off in order to detect (and subtract out) ambient light. An example from the commercially available Ohmeda model 3700 pulse oximeter is shown in FIG. 4. Sequencing the red and infrared LEDs at a frequency that is an integer multiple of the power line frequency allows the system to operate synchronously with flickering room lights. For example, fluorescent lights generate a 120 Hz flicker on 60 Hz power. The sequencing avoids potential interference of light flickers on the photodiode that would distort or disguise the tiny pulse signals of arterial pulse flow. The light timing sequence shown in FIG. 4 cycles 480 times per second at 60 Hz power; 16 of the red-infrared-off sequences are used to calculate $SaO_2$ every 0.033 second. These signals are used differently by different pulse oximeter manufacturers, as described below.

Figure 5A:
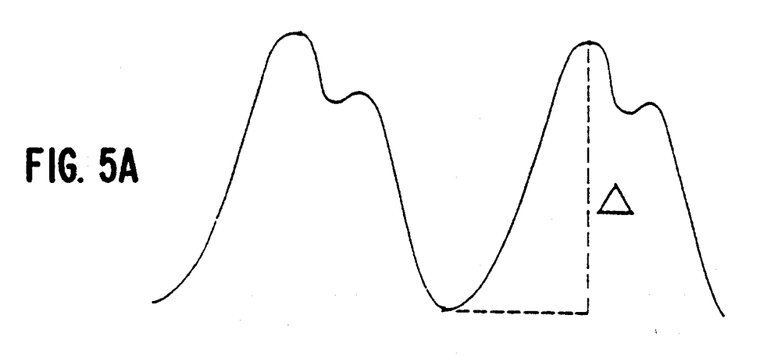
FIGS. 5A and 5B are graphs for explaining response times of pulse oximeter instrumentation.

The response time of the instrument depends on the number of data points averaged before a final $SaO_2$ reading is displayed. There are two basic approaches to this averaging, one of which relies on the time average of the peak-to-peak amplitudes of each pulse (FIG. 5A).

Figure 5B:
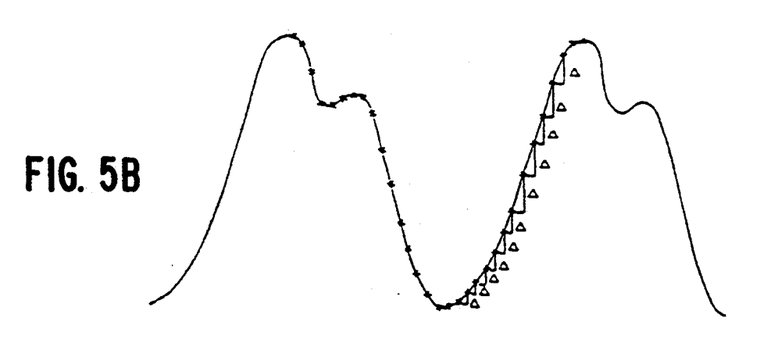

This method depends on the patient's heart rate and is relatively slow as the signals are available for averaging only once every heartbeat. Another approach is to average a large number of step changes along the steep slopes of the photoplethysmogram (FIG. 5B). In this case, the response time in the instrument is shorter because there are many more data points between successive heartbeats; also, the accuracy and stability of the measured $SaO_2$ values are usually improved by this approach. The accuracy of pulse oximeters has been extensively studied and has been found to be generally acceptable for a large number of clinical applications. Most manufacturers claim that their instruments are accurate to within $\pm 2\%$ in the $SaO_2$ range of 70–100% and within $\pm 3\%$ for $SaO_2$ values between 50 and 70%, with no specified accuracy below 50% saturation.

Most pulse oximeters offer other display features in addition to $SaO_2$, such as the pulse rate and displays to indicate the pulse waveform and relative pulse amplitude. These help the user to partially assess the quality and reliability of the measurement. For instance, if the patient's actual heart rate does not agree with that displayed by the pulse oximeter, the displayed $SaO_2$ value is brought into question. In addition, the shape and stability of the photoplethysmographic waveform often serves as an indication of possible motion artifacts.

Although pulse oximeters offer such advantageous features as described above, are now mandatory for all anesthesias and tens of thousand's of oximeters are in clinical use, doctors and hospitals have no way of knowing if the oximeters are working correctly. Until the present invention, there has not been a simple method or device for verifying oximeter operation despite a clear and pressing need. Manufacturers sometimes provide simple electronic simulators to test the electronic circuitry of their oximeters, but these do not test the performance of the optical sensor and therefore are inadequate. U.S. Pat. Nos. 4,968,137 and 5,166,517 are examples of prior art methods and devices for testing pulse oximeters.

SUMMARY OF THE INVENTION

It is a general object of the invention to provide an apparatus and method for fully determining the quality and reliability of measurements made with pulse oximeters.

It is another object of the invention to provide an apparatus and method which are suitable for testing most commercially available pulse oximeters.

These and other objects of the invention are achieved in accordance with the present invention which provides a system for simulating living tissue which is to be monitored by a pulse oximeter which provides red and infrared light flashes, the system including:
  converting the red and infrared light flashes of the pulse oximeter into electrical signals;
  modulating the converted electrical signals to provide modulated electrical signals; and
  converting the modulated electrical signals to light flashes and transmitting the converted light flashes to the pulse oximeter for detection so that the pulse oximeter responds to the converted light flashes as it would to light flashes modulated by a living tissue.

DESCRIPTION OF THE PREFERRED EMBODIMENTS

Figure 6A:
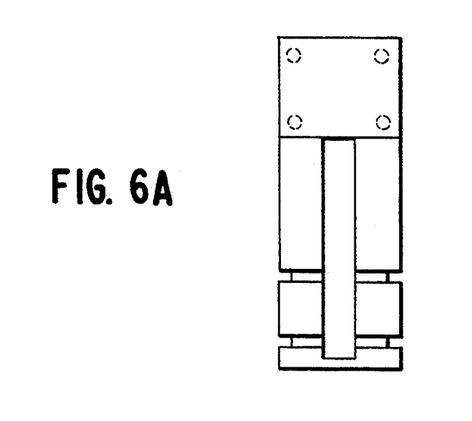
FIGS. 6A–6C are schematic diagram of an oximeter test instrument according to an embodiment of the invention.
Figure 6B:
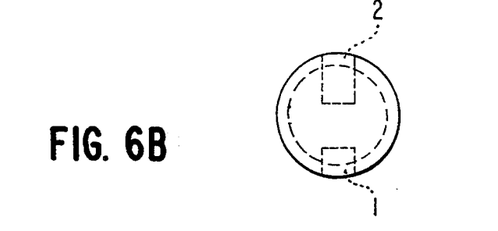
Figure 6C:
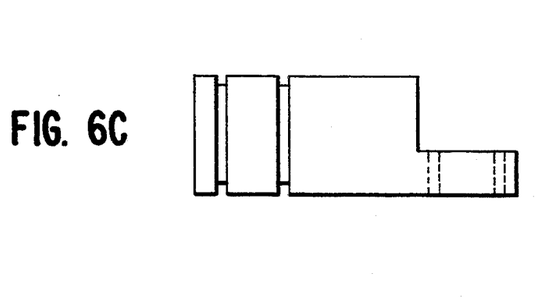

FIG. 6 is a schematic diagram of a pulse oximeter detector or test instrument according to an embodiment of the invention. The test instrument shown in FIG. 6 is intended for use with pulse oximeters employing sensors which clamp around the patient's finger. As shown in FIG. 6, the test instrument has a finger-like shape which is intended to mimic that of the patient. The test finger may be, for example, 3.5" long with a 0.75" diameter. According to this embodiment, the test instrument is fabricated from steel. Further, two long sensing photodiodes are positioned in the lower longitudinal slot 1, one diode having an infrared band pass filter so as to only receive IR, and a red LED light bar is placed in the upper longitudinal slot 2, with another photodiode placed so as to partially cover the light bar. The long, narrow shape of the test instrument (and the LED light bar) is intended to facilitate positioning of the instrument within the grip of the pulse oximeter, or the "unit-under-test" (UUT).

The flat section at the end of the "finger" provides a mechanical connection point for an analog processing circuit board. The use of a steel construction provides both opacity between the UUT light source and the UUT detector, and electrical shielding between the pulsing calibrator LED and the sensitive calibrator photodiode. It has been found that such shielding is essential to provide accurate measurements of the UUT. The round smooth sides will form a reasonably good seal with the UUT finger grip (e.g., Nellcor). Although the steel finger-shaped test instrument according to this embodiment is attached directly to the circuit board, it can be mounted at the end of a cable, much like a mouse. The electronics could then be placed within a computer, with, for example, only an photosensor preamplifier inside the "finger".

In an alternative embodiment, the steel finger-shaped test instrument is replaced with a printed circuit board cut to approximate finger width and length, with the two sensing photodiodes on the bottom surface and the LED bar with its associated photodiode mounted on the top surface. It should be noted that with a PC board it is still essential to provide opacity between the UUT light source and the UUT detector.

Figure 7:
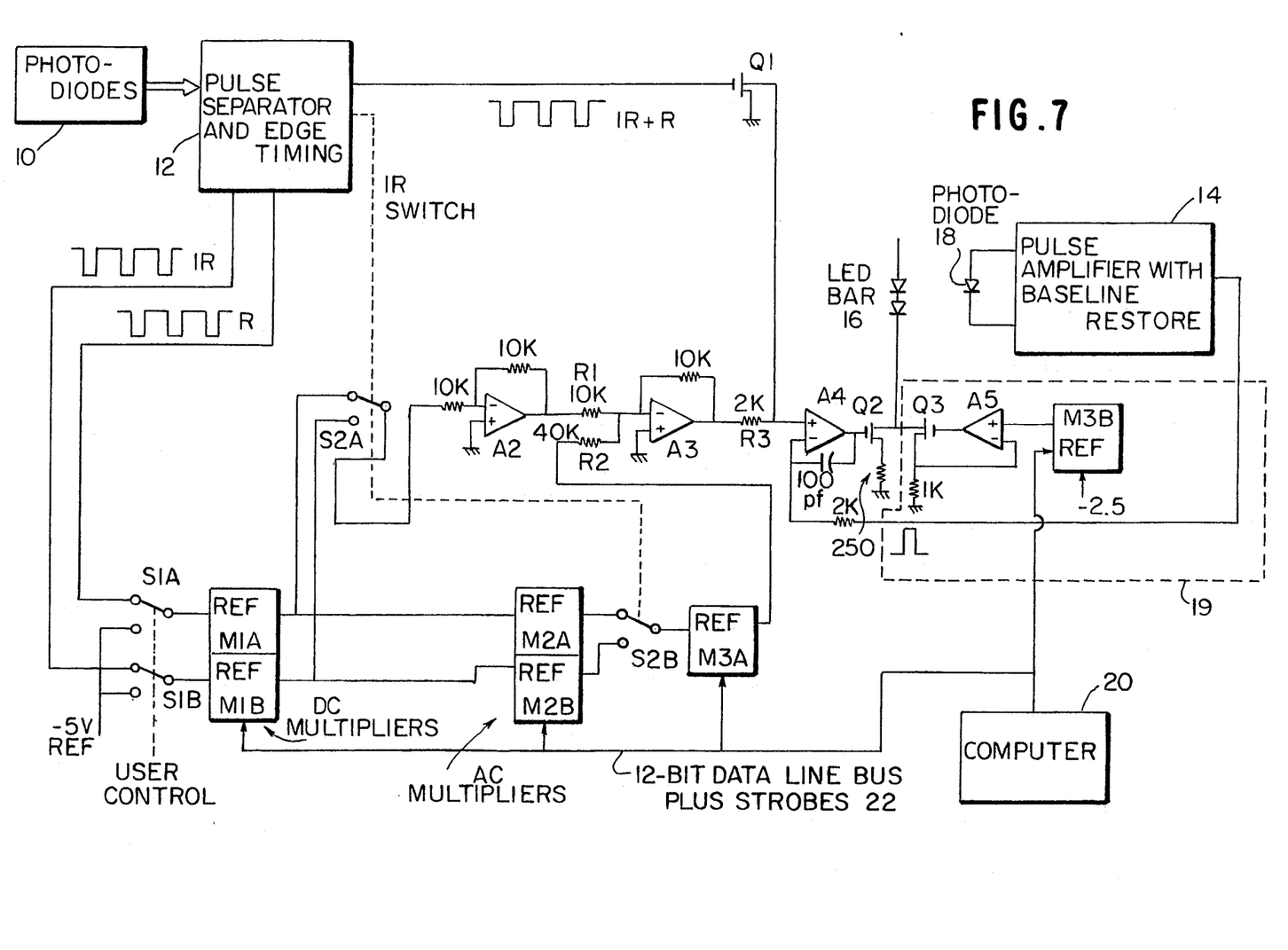
FIG. 7 is a circuit diagram of an oximeter test instrument according to an embodiment of the invention.

FIG. 7 is a circuit diagram of the oximeter test instrument according to an embodiment of the invention. As shown in FIG. 7, the circuitry includes a pair of photodiodes represented by the reference numeral 10 which feed a pulse separator and edge timing circuit 12, a pair of DC multipliers M1A, M1B which are coupled to the pulse separator and edge timing circuit 12 via a pair of switches S1A and S1B, respectively, a pair of AC multipliers M2A and M2B which are connected to receive the outputs of DC multipliers M1A and M1B, respectively, a multiplier M3A which is coupled to receive one of the outputs of AC multipliers M2A and M2B depending on the position of switch S2B, and a switch S2A which is coupled to selectively pass one of the outputs of DC multipliers M1A and M1B. As shown in FIG. 7, switches S1A and S1B are user controlled, whereas switches S2A and S2B are controlled according to an output of pulse separator and edge timing circuit 12. As will be discussed in greater detail below, switches S2A and S2B are controlled in accordance with detected IR flashes.

The circuitry shown in FIG. 7 further includes an amplifier A2 having an inverting terminal (−) which receives the signal passed by switch S2A, an amplifier A3 having an inverting terminal coupled to receive the output of amplifier A2 summed with the output of multiplier M3A, a servo amplifier A4 having a non-inverting terminal (+) coupled to receive the output of amplifier A3 and coupled to the drain of FET Q1 which has its source connected to ground and its gate coupled to receive an output of pulse separator and edge timing circuit 12, and an inverting terminal of amplifier A4 is coupled to receive an output of a pulse amplifier with baseline restore circuit 14. The circuit 14 is coupled to a photodiode 18 which detects light emitted from LED bar 16. In addition, the circuit of FIG. 7 includes a driving transistor Q2, an LED bar 16, an ambient light simulation circuit 19 and a computer 20 for controlling the DC multipliers M1A, M1B, the AC multipliers M2A, M2B, multiplier M3A and the ambient light simulation circuit 19 via a 12-bit data line bus 22. The ambient light simulation circuit 19 includes a multiplier M3B which attenuates a DC reference signal under control of computer 20, an amplifier A5 having its non-inverting terminal connected to receive an output of multiplier M3B, and a driving transistor Q3 coupled between the LED BAR 16 and the output of amplifier A5.

The operation of the circuitry shown in FIG. 7 will now be described.

In general, the circuitry of FIG. 7 uses one photodetector to capture the red and infrared pulses from the UUT, and another photodetector which is filtered such that it captures IR only, and uses the timing of these pulses to generate modulated light pulses to the UUT (i.e., pulse oximeter) via an LED bar.

The pulse separator and edge timing circuit 12 receives the outputs of the photodiodes 10, and in response thereto outputs four signals. A first signal IR Switch (represented by dotted lines) is a switch control signal for IR. This signal controls switches S2A and S2B, and is used to select the AC and DC corresponding to the infrared transmission pulse wave. That is, when the pulse separator and edge timing signal receives an IR, this signal is supplied to switches S2A and S2B to select the AC and DC corresponding to the infrared transmission pulse wave. At all other times, the red values are selected so switches S2A and S2B are in the positions shown in FIG. 7. A second signal output by circuit 12 is the red plus infrared (R+IR) pulses. As shown in FIG. 7, this signal is supplied to the gate of FET Q1. A third signal provided by circuit 12 is an electrical analog to the UUT red flash; this signal is provided to multiplier M1A via switch S1A. The fourth signal provided by circuit 12 is an electrical analog to the UUT infrared flash; this signal is supplied to multiplier M1B via switch S1B.

The circuit shown in FIG. 7 includes three multiplier chips M1A and M1B, M2A and M2B, and M3A and M3B. Each of these chips contains dual multiplying digital-to-analog converters (DACs) with internal output amplifiers. This eliminates the amplifiers and their associated components from the circuit board, and brings them within desired multiplier accuracy specifications.

The multipliers multiply by a computer-set value between 0 and −1; that is, the multipliers are both attenuating and inverting. Dual 12-bit multipliers are used for setting the finger density (DC attenuation) and creating the blood pressure wave form (AC attenuation); multipliers M1A, M1B and M2A, M2B, respectively. A single dual 8 bit multiplier is used to attenuate the AC wave (multiplier M3A) and control simulated ambient light (multiplier M3B). The switches S1A, S1B allow selection between the analogs of the UUT flashes (i.e., IR or R) and a fixed voltage (e.g., −5 V) as the DC references. When receiving the UUT light analogs, switches S1A, S1B are in the position shown in FIG. 7, and the multipliers M1A and M1B receive the R and IR analogs, respectively. However, the user is able to set switches S1A and S1B such that each of multipliers M1A and M1B receives the references signal (e.g., −5 V). This will cause the DC components of the R/IR equation (2) to drop out, thereby simplifying the equation for diagnostic purposes. The circuitry can be designed such that the selection of the UUT light analogs by switches S1A and S1B is the default choice.

The attenuated DC reference voltage (i.e., the output of multipliers M1A and M1B) becomes the reference for multipliers M2A and M2B. Further, the attenuated DC reference voltage is inverted by amplifier A2 into the range of 0 to −5 volts. The multipliers M2A and M2B serve to create the R and IR waveforms. The IR waveform has a peak multiplier setting of 1000, and the R waveform has a peak multiplier setting which varies from 400 to 3500. Multiplier M3A receives the output of either AC multiplier, depending on the position of switch S2B, and attenuate the output passing through switch S2B from its maximum value down to zero. This attenuation simulates the strength of the blood pressure wave. For example, the value zero would correspond to no heart beat. This attenuation is also for the UUT pulse loss detection test and should allow demonstration of the UUT output invariance from the highest to the lowest non-alarm AC/DC ratio.

The first element of the output stage of the circuit is amplifier A2, which inverts the positive DC levels out of multiplier M1. The inverted DC, which is now negative, is then summed with the positive AC from multiplier M3A. The DC is a negative voltage which will be proportional to base brightness, and the AC is a positive voltage representing attenuation of the blood pressure wave. The R1/R2 resistor ratio at the input of amplifier A3 sets the maximum AC at 25% of the DC applied to this summing and inverting stage. The actual AC is always less than this maximum, as the largest AC signal is only 3500/4096 times the DC out of multiplier M1A. The inverted and summed AC and DC from amplifier A3 are applied to amplifier A4 through resistor R3 and are chopped by Q1. Q1 is switched by the UUT R+IR light pulse; during the pulse, Q1 is off and amplifier A4 is driven by amplifier A3. On the other hand, when Q1 is on, the LED current (brightness) is commanded to be zero. Amplifier A4 sets the brightness for the LED bar 16 to be proportional to the input voltage of amplifier A4 when Q1 is turned off. The LED bar 16 is coupled to photodiode 18 which detects the light generated and feeds it back to amplifier A4. This is done to ensure that the LED bar output is linear. The test instrument controls the light output directly, rather than depending on the linearity and temperature stability of the LED vs. the LED current.

The ambient light simulation circuit 19 includes a multiplier M3B, an amplifier A5 and a driving transistor Q2 and serves to generate a fixed current to the LED bar in addition to the red and infrared pulses in order to simulate ambient light.

As shown in FIG. 7, the multipliers M1A, M1B, M2A, M2B, M3A and M3B are controlled by computer 20. This can be done using a simple program for setting the fixed parameters and then manipulating the R/IR ratio. The various control parameters for the multipliers are described below.

In order to provide the DC, or non-pulsatile, level, the circuit includes the multipliers M1A and M1B which cover the range from opaque to transparent, and is settable by the computer 20 over this range in 4,096 steps. Also, computer 20 is able to set the red and infrared DC attenuation (i.e., multipliers M1A and M1B) separately.

In order to provide the AC, or pulsatile, level, the circuit includes the multipliers M2A and M2B. As indicated above, these multipliers create the R and IR waveforms, with the IR waveform having a peak multiplier setting of 1000, and the R waveform having a peak multiplier setting which varies from 400 to 3500.

As shown in FIG. 3, the red to infrared ratio (R/IR) ratio can range from 0.4 to 3.4, corresponding to 100% and 0% $SaO_2$, respectively. Pulse oximeters have approximately 1% resolution; in order to effectively calibrate such an instrument, the calibrator should be several times better, preferably an order of magnitude. Therefore, the circuit employs a 12-bit multiplying digital-to-analog converter (DAC), which will provide 0.1% (or better) resolution of the full wave amplitude over the range of R/IR values from 0.4 to 3.5. The tracking accuracy between the two sections of the DAC chip is one bit or better.

The AC to DC ratio corresponds to the strength of the blood pressure wave, and this ratio is simulated by multiplier M3A. One of the tasks of a pulse oximeter is to sound an alarm if the blood pressure wave is lost. Therefore, an important question is: "At what level of wave weakness is the alarm tripped?" The computer 20 is able to set the wave amplitude (i.e., multiplier M3A) from zero up to approximately 20% of the DC level in 256 steps.

A blood pressure wave corresponding to one heart beat is generated by the computer 20 feeding the AC multipliers M2A, M2B a series of 64 numbers corresponding to blood pressure amplitude, starting at zero and returning to zero. The series of 64 numbers then repeats to form the next beat. The 64 numbers are selected such that if the series of numbers were plotted against time, then the resulting curve would be a blood pressure wave corresponding to one heart beat. A simulated heart rate is established by the computer 20 setting the time between the presentation of each of the 64 numbers. For example, if they are presented to the multipliers 1/64th of a second apart, the full wave takes one second to generate, corresponding to 60 beats/minute. The computer 20 can readily set the time between multiplier settings so that any reasonable simulated heart rate can be established. A simulated heart rate range of between 30 and 240 bpm should be adequate for most applications.

As indicated above, the ambient light simulation circuit 19 serves to drive the LED bar 16 in order to simulate ambient light. Computer 20 controls multiplier M3B of circuit 19 so as to allow for a settable minimum dc current through the LED bar 16.

Figure 8:
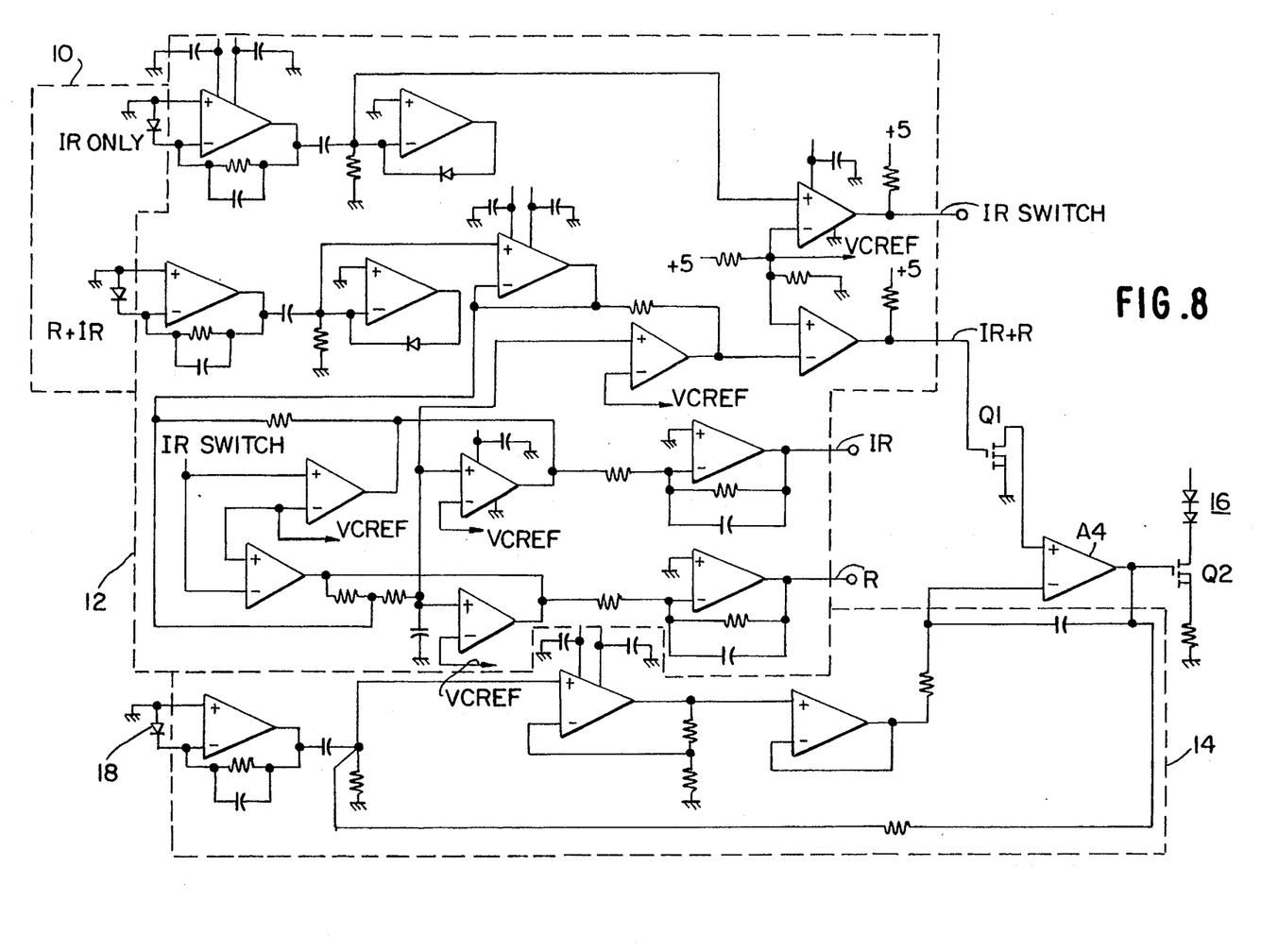
FIG. 8 is a circuit diagram showing elements of the circuit of FIG. 7 in greater detail.

FIG. 8 shows the pulse separator and edge timing circuit 12 and the pulse amplifier with baseline restore circuit 14 of FIG. 7 in greater detail. As shown in FIG. 8, the photodiodes 10 include a first diode for receiving both R and IR, and a second diode which is filtered so as to receive only IR, and the outputs of the diodes are supplied to the pulse separator and edge timing circuit 12. As shown in FIG. 8, circuit 12 comprises several amplifiers, comparators and buffers which are connected as shown so as to output four different signals. Specifically, circuit 12 outputs a signal representing R+IR, a signal representing IR only, a signal representing R only and the IR switch control signal. As shown in FIG. 8, the IR+R signal is supplied to the gate of chopping transistor Q1 which has its drain connected to the non-inverting terminal of servo amplifier A4 whose output drives the LED bar 16 via driving transistor Q2. As also shown in FIG. 8, the pulse amplifier receives the output of photodiode 18 (which is disposed so as to sit on the LED BAR 16) and includes several amplifiers and buffers. As discussed above, the circuit 14 provides an output to the inverting terminal of servo amplifier A4, thereby providing closed loop control of the LED BAR 16.

As set forth above, the device and method according to the present invention is able to simulate a living tissue, such as a finger, thereby enabling testing of a pulse oximeter by comparing the parameters of the simulated living tissue with the parameters obtained from the pulse oximeter under test.

Although the present invention has been shown and described with reference to particular embodiments, various changes and modifications as apparent to those skilled in the art can be made without departing from the true scope and spirit of the invention as defined in the claims.

What is claimed is:

1. A method for simulating living tissue which is to be monitored by a pulse oximeter that provides red and infrared light flashes, the method comprising:
   a. converting the red and infrared light flashes of the pulse oximeter into electrical signals;
   b. modulating the converted electrical signals to provide modulated electrical signals; and
   c. converting the modulated electrical signals to light flashes and transmitting the converted light flashes to the pulse oximeter for detection so that the pulse oximeter responds to the converted light flashes as it would to light flashes modulated by a living tissue.

2. The method as defined in claim 1, further comprising the step of blocking the red and infrared light flashes produced by the oximeter from being directly detected by the pulse oximeter.

3. The method as defined in claim 1, further comprising the steps of:
   converting the brightness of each light flash created in step (c) into a proportional electrical signal;
   comparing said proportional electrical signal to the amplitude of the modulated electrical signal formed in step (b); and
   adjusting the light intensity of the light flash formed in step (c) so as to null out any difference between said proportional electrical signal and said modulated electrical signal.

4. An apparatus for simulating living tissue which is to be monitored by a pulse oximeter that provides red and infrared light flashes, the apparatus comprising:

first means for converting the red and infrared light flashes of the pulse oximeter into electrical signals;

second means for modulating the converted electrical signals to provide modulated electrical signals; and third means for converting the modulated electrical signal to light flashes and transmitting the converted light flashes to the pulse oximeter for detection so that the pulse oximeter responds to the converted light flashes as it would to light flashes modulated by a living tissue.

5. The apparatus as defined in claim 4, further comprising means for blocking the red and infrared light flashes produced by the oximeter from being directly detected by the pulse oximeter.

6. The apparatus as defined in claim 4, further comprising:

means for converting the brightness of each light flash created by said first means into a proportional electrical signal;

means for comparing said proportional electrical signal to the amplitude of the modulated electrical signal formed by said second means; and means for adjusting the light intensity of the light flash formed in said third means so as to null out any difference between said proportional electrical signal and said modulated electrical signal.

7. The system of claim 4, wherein the means for converting the red and infrared light flashes of the pulse oximeter into electrical signals comprises photodiode detector means, amplification means, signal coupling means which removes the dc component from the amplified photodiode electrical signal, and dc restorer means to reference said photodiode electrical signal to a fixed level, regardless of photodiode output due to ambient light.

8. The system of claim 4, wherein said modulating means for modulating said electrical signals comprises a plurality of multipliers.

* * * * *